United States Patent [19]
Hsia

[11] Patent Number: 6,009,340
[45] Date of Patent: Dec. 28, 1999

[54] MULTIMODE, MULTISPECTRAL IMAGING SYSTEM

[75] Inventor: Yukun Hsia, Santa Ana, Calif.

[73] Assignee: Northrop Grumman Corporation, Los Angeles, Calif.

[21] Appl. No.: 09/039,968

[22] Filed: Mar. 16, 1998

[51] Int. Cl.[6] .................................................. A61B 5/05
[52] U.S. Cl. .................. 600/407; 600/473; 600/476; 358/113
[58] Field of Search .................... 600/473, 474, 600/476; 364/413, 414, 115; 382/6, 22; 358/113

[56] References Cited

U.S. PATENT DOCUMENTS

| | | | |
|---|---|---|---|
| 4,170,987 | 10/1979 | Anselmo et al. | 128/665 |
| 4,515,165 | 5/1985 | Carroll | 128/664 |
| 4,515,615 | 5/1985 | Eastin | 71/54 |
| 4,599,001 | 7/1986 | Richard | 356/419 |
| 4,671,298 | 6/1987 | Babb et al. | 128/719 |
| 4,751,571 | 6/1988 | Lillquist | 358/113 |
| 4,953,111 | 8/1990 | Yamamoto et al. | 364/569 |
| 4,962,357 | 10/1990 | Sotak | 324/309 |
| 5,003,979 | 4/1991 | Merickel et al. | 128/653 |
| 5,016,173 | 5/1991 | Kenet et al. | 364/413.13 |
| 5,038,786 | 8/1991 | Kojima | 128/653 |
| 5,078,150 | 1/1992 | Hara et al. | 128/665 |
| 5,088,493 | 2/1992 | Giannini et al. | 128/633 |
| 5,101,825 | 4/1992 | Gravenstein et al. | 128/633 |
| 5,213,105 | 5/1993 | Gratton et al. | 128/664 |
| 5,218,207 | 6/1993 | Rosenthal | 250/341 |
| 5,219,400 | 6/1993 | Jacot et al. | 128/633 |
| 5,219,413 | 6/1993 | Lineberger | 180/272 |
| 5,222,496 | 6/1993 | Clarke et al. | 128/633 |
| 5,251,632 | 10/1993 | Delpy | 128/633 |
| 5,257,625 | 11/1993 | Pelc | 128/653.2 |
| 5,261,404 | 11/1993 | Mick et al. | 128/653.1 |

*Primary Examiner*—Marvin M. Lateef
*Assistant Examiner*—Ali M. Imam
*Attorney, Agent, or Firm*—Terry J. Anderson; Karl J. Hoch, Jr.

[57] ABSTRACT

A multispectral imaging system for generating imagery from a broad range of electromagnetic radiation. In a preferred embodiment, the system comprises an image processor unit having a plurality of dedicated inputs formed thereon, each of which connectable to a respective one of a plurality of sensors wherein each sensor is designed to detect wavelengths emanating from a specific spectral region. The image processor unit receives data from a respective sensor, processes such data, and generates an output that is fed to a multimedia controller and computer, the latter being designed to either digitally store, display or provide a printout of the imaging data. In a preferred embodiment, the multimedia controller computer is further designed to transfer such imagery data to a variety of data links to users interfacing with the imaging system. The system may further be modified to accommodate endoscopic sensors for use in procedures related thereto.

12 Claims, 1 Drawing Sheet

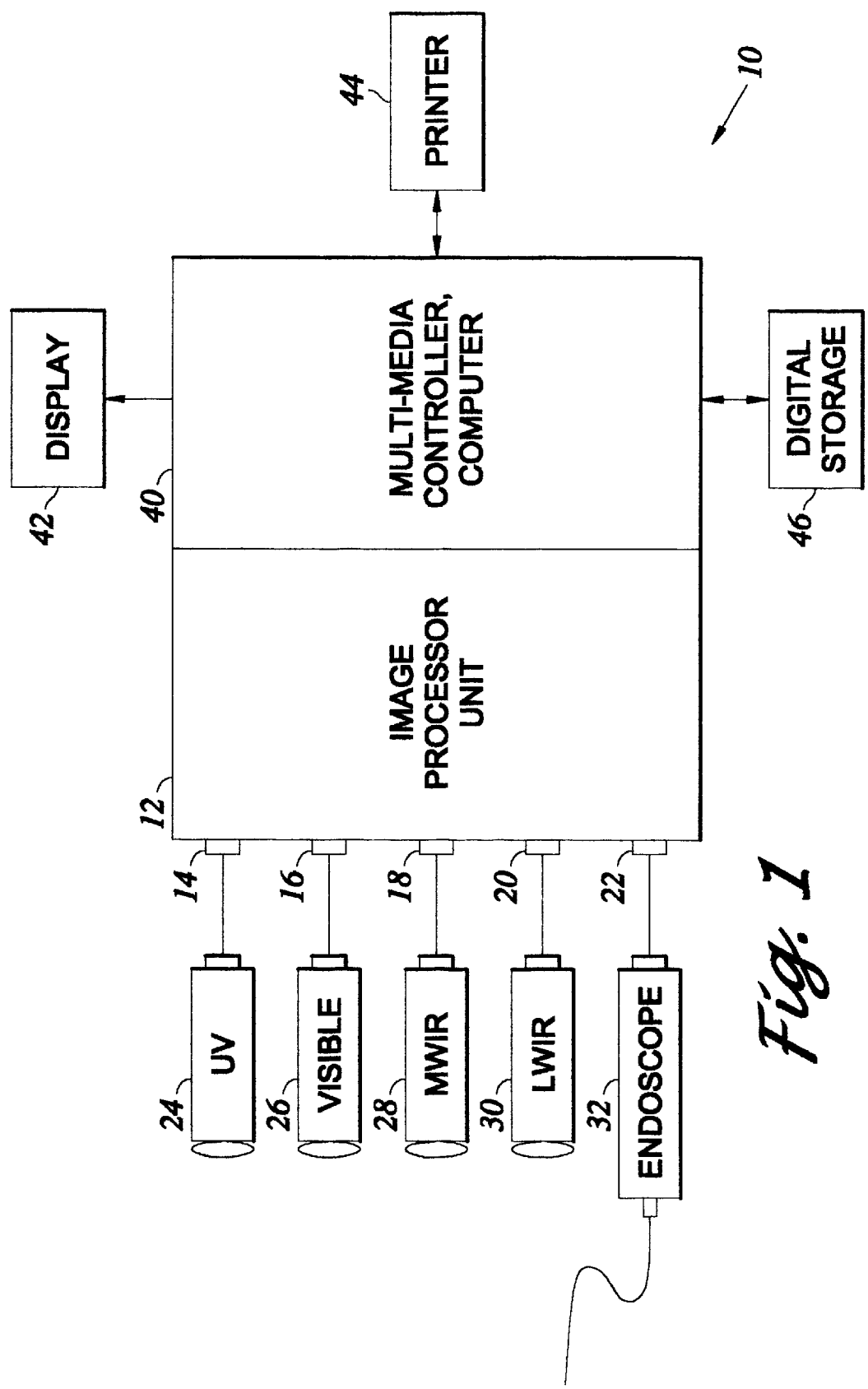

MULTIMODE, MULTISPECTRAL IMAGING SYSTEM

FIELD IF THE INVENTION

The present invention relates generally to medical imaging systems, and more particularly, multimode, multifunctional medical imaging systems utilizing an imaging spectrum spanning from UV light, through visible light, to mid and longwave infrared light.

BACKGROUND OF THE INVENTION

Medical imaging devices are well known to those skilled in the art. Such systems typically use the transmission and reflection of radiation to detect the internal structure underlying the skin. Thermographic techniques are also extensively utilized in the interrogation of human tissue, which detect the differences in temperature and the different tissue types in the body portions examined. Such system typically utilizes infrared radiation detectors to detect the different degrees of infrared radiation emitted by heated bodies. Images are also generated by such systems by using visible and infrared radiation. Still further, ultraviolet (UV) radiation is frequently utilized for purposes of defining an area of malignancy/anomaly for surgery, as well as detect the presence of early cancerous and pre-cancerous tissues.

Notwithstanding their utility, most imaging systems in use today are typically specific to limited spectral bands. In this respect, imaging systems are typically dedicated to a select spectral band, for example, visible or infrared, and thus can only be utilized for limited types of procedures. For example, thermographic techniques must typically be performed via infrared radiation imaging systems, whereas techniques requiring the application of UV radiation, as is frequently utilized in certain tumor screening procedures, must necessarily be performed with a dedicated UV imaging system.

While attempts have been made to develop imaging systems that are capable of using a radiation/light source having wavelengths covering a particular spectral band, such as those disclosed in U.S. Pat. No. 4,515,615 to Carroll entitled *Apparatus and Method for Detecting Tumors* and U.S. Pat. No. 5,088,493 to Giannini et al. entitled *Multiple Wavelencth Light Photometer for Non-Invasive Monitoring*, such systems nonetheless cover exceptionally narrow spectral bands. For example, the system disclosed in U.S. Pat. No. 4,515,615 is designed to cover wavelengths ranging only from 400 nanometers to 4,000 nanometers. Similarly, the system disclosed in U.S. Pat. No. 5,088,493 is limited to covering wavelengths ranging from approximately 750 nanometers to 900 nanometers.

Accordingly, there is a need in the art for a medical imaging system that is designed to accommodate an imaging spectrum that spans from the ultraviolet through visible mid and longwave infrared wavelengths. In this regard, it would be advantageous to provide an imaging system that, by virtue of its capability to accommodate and provide image processing for several spectral regions, is capable of providing diagnostic medical imaging in a multimode, multi-functional manner that eliminates the need for multiple prior art imaging systems designed to accommodate specific, narrow spectral bands. Specifically, it would be advantageous to provide a single imaging system for use in diagnostics, intraoperative procedure control and monitoring, as well as effective early detection of tumors and the like that currently must be performed by a plurality of imaging systems. There is still further a need for a multifunctional, multispectral imaging system that is capable of being utilized in a wide variety of medical applications that is readily adaptable to existing technology that further lowers the cost and provides the equivalent or greater reliability of most medical imaging systems currently in use.

SUMMARY OF THE INVENTION

The present invention specifically addresses and alleviates the above-deficiencies in the art. In this regard, the present invention is directed to a spectroscopic imaging system designed to accommodate and detect a plurality of spectral regions for producing a composite visible/thermal-infrared image for use in diagnostic and intraoperative procedures. In a preferred embodiment, the system comprises an image processor unit having a plurality of dedicated input ports formed thereon for connecting with a plurality of spectral sensors wherein each respective sensor detects a range of wavelengths falling within a specific spectral band. The image processor unit is designed to take sensor data provided by any of the respective sensors utilized in a given imaging procedure, via traditional image signal processing, and process the data to produce an output, the latter being managed by multimedia controller and computer, to thus subsequently generate either graphic storage, display, and/or hard copy printing, as well as data telecommunication via a variety of data links to users of the system. In a preferred embodiment, an image processor unit is provided with at least four input ports dedicated to interconnect with sensors responsive to ultraviolet, visible and near infrared, midwave infrared, and longwave infrared radiation. In a further refinement of the present invention, the image processor unit may further include dedicated input ports for interconnecting with conventional endoscopic sensors to thus increase the number of applications and techniques for which this system may be utilized.

It is therefore an object of the present invention to provide a multispectral imaging system capable of detecting multiple spectral bands ranging across a wider range of the electromagnetic spectrum than prior art devices.

Another object of the present invention is to provide a multispectral imaging system that is capable of producing substantially greater multispectral imagery than prior art imaging systems.

Another object of the present invention is to provide a single imaging system capable of detecting radiation from a broader image of spectral regions, including ultraviolet, visible and near infrared, midwave infrared, and longwave infrared, than prior art imaging systems.

Another object of the present invention is to provide multispectral imaging system that is further designed and adapted for utilization in endoscopic applications.

A still further object of the present invention is to provide a multispectral imaging system that can be used with conventional imaging equipment, can perform a wider range of imagery than prior art systems, can eliminate the need for a plurality of imaging systems dedicated to particular spectral regions, and can enable medical imaging procedures to be performed at lower cost than prior art imaging systems.

BRIEF DESCRIPTION OF THE DRAWINGS

FIG. 1 is a block diagram of the components comprising the multispectral imaging system of the present invention.

DETAILED DESCRIPTION OF THE PREFERRED EMBODIMENT

The detailed description set forth below in connection with the appended drawing is intended merely as a description of the presently preferred embodiment of the invention, and is not intended to represent the only form in which the present invention may be constructed or utilized. The description sets forth the functions and sequence of steps for construction and implementation of the invention in connection with the illustrated embodiment. It is to be understood, however, that the same or equivalent functions and sequences may be accomplished by different embodiments that are also intended to be encompassed within the spirit and scope of the invention.

Referring now to FIG. 1, there is schematically illustrated the components of a multispectral imaging system 10 as constructed according to a preferred embodiment of the present invention. As illustrated, the system 10 comprises an image processor unit 12 having a plurality of inputs 14, 16, 18, 20 and 22 formed thereon for interconnecting with respective ones of a plurality of sensors 24, 26, 28, 30 and 32. As shown, each of the respective sensors, but for endoscopic sensor 32 discussed more fully below, are designed to detect radiation from a specific spectral region. More specifically, a first respective sensor 24 is designed to detect radiation having wavelengths falling within the ultraviolet region of the electromagnetic spectrum, whereas a respective second sensor 26 detects those wavelengths falling within the visible and near infrared spectral region. Third and fourth sensors 28 and 30, respectively, are preferably designed to detect midwave and longwave infrared radiation wavelengths.

According to one preferred embodiment, the multispectral imaging system 10 of the present invention, and more particularly the respective sensors 24–30 utilized therewith, is responsive to and may be utilized for imaging procedures utilizing electromagnetic radiation falling within one of four specific spectral regions of ultraviolet, visible and near infrared, midwave infrared, and longwave infrared radiation. In a preferred embodiment, first sensor 24 will detect ultraviolet radiation having wavelengths ranging from 250–400 nanometers and second sensor 26 will detect visible and near infrared radiation having wavelengths extending from 400 nanometers to 1 micrometer. Third sensor 28, designed to detect midwave infrared radiation, preferably detects such radiation having wavelengths between 3–5 micrometers and fourth sensor 30 will preferably detect longwave infrared radiation having wavelengths between 8 and 12 micrometers.

As will be recognized by those skilled in the art, the aforementioned sensors utilized to detect the various spectral regions identified above may take any of a variety of devices currently available. For example, one preferred ultraviolet radiation sensor comprises a Gen II+(UV) photocathode image intensifier, coupled with a fiber optic minifier and CCD FPA in connection with advanced video electronics to result in a high sensitivity, 12 orders of magnitude dynamic range, multifunction, multispectral UV video camera. Similarly, in the case of the imaging midwave infrared sensor 28, a 128×128 imaging sensor array may be utilized. Still further, visible radiation detector 26 may comprise any conventional imaging detector of visible light, such as a solid state CCD or CDI detector array, or a vidicon tube. Such visible radiation detector 26 may also comprise any conventional imaging detector of visible light whose low light lower response characteristics have been augmented by the addition of an electro-optic image intensifier device.

The signal received from the respective sensors is then processed by the image processor unit 12. The image processor unit 12 provides for sensor fusion, pattern recognition and other traditional image signal processing capabilities well known to those skilled in the art. Advantageously, however, the image processor unit 12 employs an open architecture, and more specifically, interconnect-intensive parallel architecture that enables the same to operate in multimode, multifunctional modular capacity unlike prior art devices. In this regard, it should be understood that such open system architecture referenced herein mimics, and is in fact a conversion of, battlefield tested aerospace multispectral imaging technology which incorporates existing state of the art military sensor hardware but converts and applies the same for use in medical electro-optic applications. Accordingly, the respective outputs of each of the sensors 24–30 connectable to the image processor unit 12 is capable of being received and processed thereby and a corresponding image generated therefrom that cannot be otherwise be done, to date, with current prior art devices that are specific for a particular diagnostic modality.

Such open architecture further enables the image processor unit to be utilized in further electro-optic applications, and in particular endoscopic applications. As illustrated, image processor unit 12 is provided with an input 22 for interconnecting with a conventional endoscopic device 32, such as vascular endoscopes and the like, to thus enable the system 10 to achieve greater flexibility and thus enables the same to be utilized in a greater number of medical procedures.

The system 10 further includes a multimedia controller and computer 40 that is designed to receive the output from the image processor unit 12 and generate graphic imagery data for use in evaluation in any of a plurality of diagnostic or intraoperative procedures. As is well know to those skilled in the art, the multimedia controller and computer 40 may be coupled to either a video display 42, a printer 44 or even a storage or memory 46 such that the resultant imagery data can be evaluated as desired. More specifically, such multimedia controller and computer 40 will specifically be designed so that graphic storage, display, and hard copy printing will be available to the user, as per conventional imaging systems. Furthermore, although not shown, such multimedia controller and computer 40 may further be designed to transmit imagery data via a variety of data links to users interfacing with the system as may be desired. As such, the multispectral imaging system 10 of the present invention not only is capable of being utilized to conduct numerous imaging techniques and procedures utilizing spectral bands extending across a greater portion of the electromagnetic spectrum than prior art devices, but is further capable of generating an imaging output that may be manipulated in any of a number of ways to thus offer the greatest amount of flexibility to the users of such system 10.

To stress such a flexibility of the multispectral imaging system 10 of the present invention, there is provided herebelow a variety of imaging techniques that may be performed via the multispectral imaging system 10 of the present invention that to date cannot otherwise be performed by a single imaging device. With respect to those techniques performed using ultraviolet radiation, and more particularly, radiation having a wavelength from between 250–400 nanometers, the system of the present invention may be utilized to define areas of malignancy or anomaly for surgery, and hence early detection of cancerous and precancerous tissues, as well as the determination of a specific form of lupus erythematosus. Such UV sensor may be further be fused with sensor data from the infrared sensor to enhance such aforementioned imaging techniques. Likewise, such UV spectral band may be fused with data received from the visible sensor for use in forensic and legal applications and counter immune electrophoresis for immunosorbent assay.

With respect to those imaging procedures utilizing visible and near-infrared radiation, such would include non-invasive monitoring of intraoperative cardiac preservation, real-time, immediate evaluation of the procedure success during reperfusion, and comprehensive, real-time measurement of ischemia. Further applications could include documentation for postoperative analysis.

The imaging system of the present invention can further be utilized for non-invasive, low cost thermalgraphy to supplement a mammography. The system may further be utilized during hypothermic neurosurgery for temperature monitoring and procedure control. Additional applications include the diagnosis of malignant melanoma and determination of sarcoma, as well as treatment progress related thereto. The imaging system may further be utilized to monitor patient temperature in hypothermic and hyperthermic procedures, as well as postoperative monitoring of free tissue transfers and reconstructive microsurgery. Further applications include muscular skeletal monitoring and diagnosis related to nerve root diseases, arthritis and inflammation.

It should be understood, however, that the aforementioned applications for use of the imaging system 10 of the present invention is only exemplary and by no means exhaustive. In this regard, it should be understood that numerous other imaging techniques may be performed by the imaging system 10 of the present invention and that future procedures and techniques will undoubtedly be developed in the future for which the system 10 may be utilized.

What is claimed is:

1. A multispectral imaging apparatus for non-invasive monitoring of a body organ in vivo comprising:
    a) a plurality of radiation sensor devices for detecting radiation from a scene of said body organ wherein each respective sensor detects a range of wavelengths falling within a spectral band selected from the group consisting of ultraviolet, visible, near infrared, midwave infrared, and longwave infrared radiation and generating a signal corresponding thereto;
    b) an image processor unit having a plurality of dedicated input ports formed thereon for connecting with respective ones of said sensors, said image processor unit being operable to simultaneously receive data from at least two of said sensors from at least two dissimilar spectral bands wherein at least one of the spectral band is ultraviolet, and process said signals generated by said sensors and convert said signals to imagery data related to said scene of said organ;
    c) a multimedia controller electrically connected to the image processor unit for receiving said imagery data therefrom and displaying an image of said scene.

2. The apparatus from claim 1 wherein said sensor responsive to ultraviolet radiation is responsive to wavelengths ranging from 250 to 400 nanometers.

3. The apparatus from claim 1 wherein said sensor responsive to midwave infrared sensor is responsive to wavelengths ranging from 3 to 5 micrometers.

4. The apparatus from claim 1 wherein said sensor responsive to longwave infrared sensor is responsive to wavelengths ranging from 8 to 12 micrometers.

5. The apparatus from claim 1 wherein said system includes a sensor responsive to visible and near infrared radiation having wavelengths ranging from 400 nanometers to 1 micrometer.

6. The apparatus of claim 1 wherein said multimedia controller is further operable to store and retrieve said imagery data received from said image processor unit.

7. The apparatus of claim 1 further comprising:
    d) a printer connectable to said multimedia controller for printing imagery data related to said scene of said organ.

8. A method for non-invasively generating images of a scene of a body organ in vivo comprising the steps:
    a) detecting radiation reflected from said scene of said body organ by at least two of a plurality of sensors wherein one of said sensors is designed to detect ultraviolet radiation and the respective other sensor is designed to detect a wavelength falling within a specific spectral band selected from the group consisting of visible, near infrared, midwave infrared, and longwave infrared radiation;
    b) generating first and second signals corresponding to said reflected radiation detected by at least two of said plurality of sensors;
    c) fusing said first and second signals to produce a resultant signal;
    d) processing and converting said resultant signal to medical image data related to said scene of said organ; and
    e) generating a visual image of said scene of said organ from medical image data.

9. Method of claim 8 wherein in step a), said sensors are provided to detect radiation falling within ultraviolet, visible and near infrared, midwave infrared, and longwave infrared spectral regions.

10. Method of claim 9 wherein in step a), said ultraviolet spectral region ranges from 250 to 400 nanometers, said visible and near infrared spectral region ranges from 400 nanometers to 1 micrometer, said midwave infrared spectral region ranges from 3 to 5 micrometers and said longwave infrared spectral region ranges from 8 to 12 micrometers.

11. The method of claim 8 wherein in step d), said imagery data received from step c) is stored into a memory.

12. The method of claim 8 wherein in step d), said imagery data is printed out via a printer.

* * * * *